United States Patent
Wang et al.

(10) Patent No.: US 6,664,333 B2
(45) Date of Patent: *Dec. 16, 2003

(54) COLD-WATER FLUSHABLE COMPOSITIONS COMPRISING POLYLACTIC ACID DISPERSED IN POLYVINYL ALCOHOL

(75) Inventors: James Hongxue Wang, Appleton, WI (US); David Michael Schertz, Roswell, GA (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/259,429

(22) Filed: Mar. 1, 1999

(65) Prior Publication Data

US 2002/0065363 A1 May 30, 2002

Related U.S. Application Data

(63) Continuation-in-part of application No. 08/774,730, filed on Dec. 31, 1996, now abandoned.

(51) Int. Cl.$^7$ .............................. C08L 29/04; C08L 67/04
(52) U.S. Cl. ........................... 525/58; 524/27; 524/35; 524/47; 525/167; 525/175; 525/186; 525/190; 525/408; 525/411; 525/425; 525/437
(58) Field of Search ........................ 525/58, 167, 175, 525/176, 186, 190, 408, 411, 425, 437; 524/27, 35, 47

(56) References Cited

U.S. PATENT DOCUMENTS

| | | | |
|---|---|---|---|
| 3,806,495 A | | 4/1974 | Schoen |
| 4,284,671 A | | 8/1981 | Cancio et al. |
| 4,504,635 A | | 3/1985 | Weber, Jr. et al. |
| 4,526,938 A | | 7/1985 | Churchill et al. |
| 4,620,999 A | | 11/1986 | Holmes |
| 4,683,287 A | | 7/1987 | Koleske et al. |
| 4,701,483 A | | 10/1987 | Okitsu |
| 4,745,160 A | | 5/1988 | Churchill et al. |
| 4,767,829 A | | 8/1988 | Kordomenos et al. |
| 4,826,493 A | | 5/1989 | Martini et al. |
| 4,826,945 A | | 5/1989 | Cohn et al. |
| 4,921,934 A | | 5/1990 | Bixler et al. |
| 4,933,182 A | | 6/1990 | Higashi et al. |
| 5,136,017 A | | 8/1992 | Kharas et al. |
| 5,196,247 A | * | 3/1993 | Wu .............................. 428/43 |
| 5,200,247 A | | 4/1993 | Wu et al. |
| 5,278,202 A | | 1/1994 | Dunn et al. |
| 5,300,576 A | | 4/1994 | Nemphos et al. |
| 5,322,925 A | | 6/1994 | Muth et al. |
| 5,342,659 A | | 8/1994 | Horowitz et al. |
| 5,360,892 A | | 11/1994 | Bonsignore et al. |
| 5,391,423 A | * | 2/1995 | Wnuk ........................ 428/217 |
| 5,410,016 A | | 4/1995 | Hubbell et al. |
| 5,417,983 A | | 5/1995 | Nagase et al. |
| 5,422,387 A | | 6/1995 | Toms et al. |
| 5,434,241 A | | 7/1995 | Kim et al. |
| 5,470,944 A | | 11/1995 | Bonsignore |
| 5,472,518 A | | 12/1995 | Patnode et al. |
| 5,508,101 A | | 4/1996 | Patnode et al. |
| 5,525,671 A | | 6/1996 | Ebato et al. |
| 5,567,435 A | | 10/1996 | Hubbell et al. |
| 5,567,510 A | | 10/1996 | Patnode et al. |
| 5,574,129 A | | 11/1996 | Miyoshi et al. |
| 5,583,187 A | | 12/1996 | Sharak et al. |
| 5,612,052 A | | 3/1997 | Shalaby |
| 5,654,381 A | | 8/1997 | Hrkach et al. |
| 5,658,977 A | | 8/1997 | Yang et al. |

FOREIGN PATENT DOCUMENTS

| | | |
|---|---|---|
| EP | 241178 | 10/1987 |
| EP | 0654504 | 4/1995 |
| EP | 0704470 | 3/1996 |
| JP | 6-142127 | 5/1994 |
| JP | 6-298921 | 10/1994 |
| JP | 8-239457 | 9/1996 |
| WO | 92/04412 | 3/1992 |
| WO | 94/10257 | 5/1994 |
| WO | 98/29506 | 7/1998 |

OTHER PUBLICATIONS

Williams et al. Biodegradable Plastics from Plants *Chemtech* 38–44 1996.

Ikejima, T., et al. Infrared Analysis on Blends of Poly (3–Hydrooxybutyric Acid) and Stereoregular Poly (Vinyl Alcohol): Influence of Tecticity of Poly (Vinyl Alcohol) on Crystallization of Poly (3–Hydroxybutyric Acid) *Macromolecular Chemistry and Physics* 197(3 869–880) 1996.

* cited by examiner

*Primary Examiner*—Patricia A. Short
(74) *Attorney, Agent, or Firm*—Brinks Hofer Gilson & Lione

(57) ABSTRACT

Selectively cold-water responsive compositions constructed of combinations of polymers including at least one hydrolytically degradable polymer and at least one cold-water soluble polymer are provided. Additionally, methods of making and using selectively cold-water sensitive compositions are described. In one embodiment, the method comprises combining a polylactide and a cold-water soluble polyvinyl alcohol at a temperature above the melting point of the polymer having the higher melting point, and below the decomposition point of the polymer having the lower decomposition point, to form a homogeneous polymer blend is also provided. The cold-water responsive properties of the compositions of the present invention may be varied include water dispersible, water disintegratable, and water weakenable.

5 Claims, 1 Drawing Sheet

COLD-WATER FLUSHABLE COMPOSITIONS COMPRISING POLYLACTIC ACID DISPERSED IN POLYVINYL ALCOHOL

This application is a continuation-in-part of application U.S. Ser. No. 08/774,730 filed Dec. 31, 1996, now abandoned.

FIELD OF THE INVENTION

The present invention relates to cold-water responsive compositions and methods of manufacturing and using cold-water responsive compositions. The cold-water responsive compositions of the present invention have a wide range of cold-water responsiveness ranging from cold-water dispersible to cold-water weakenable. The cold-water responsive compositions of the present invention comprise a blend of a hydrolytically degradable polymer such as polylactic acid and at least one cold-water responsive polymer such as polyvinyl alcohol. The compositions of the present invention are responsive to water at ambient temperature and conditions are particularly suited for use in the manufacture of a variety of disposable products.

BACKGROUND OF THE INVENTION

Even though the amount of plastics used in a variety of consumer goods, packaging and medical articles has not significantly increased over the past twenty years, the common perception is that more and more plastics are filling up our landfills. Plastics offer many advantages over the more traditional wood, glass, paper, and metal articles including improved performance, comparable or decreased cost of manufacture and decreased transportation costs. Disposal of all waste materials, including food waste, packaging materials, medical waste into a typical landfill provides a relatively stable environment in which none of these materials is seen to decompose at an appreciable rate. Alternative waste disposal options are increasingly discussed and utilized to divert some fractions of waste from entombment. Examples of these alternatives include municipal solid waste composting, anaerobic digestion, enzymatic digestion, and waste water sewage treatment.

Much controversy is associated with the disposal of medical waste. Both government agencies and members of the public sector have been increasingly directing in-depth scrutiny toward this subject. Admittedly, concerns over the fate of materials contaminated with infectious substances are valid and proper measures to insure the safety of health care workers and the general public should be taken.

Currently, medical waste can be categorized into reusable and disposable. Categorization as to whether certain waste is reusable or disposable is customarily determined according to the material from which the article was constructed and the purpose for which the article was used.

After use, reusable medical articles are cleansed and sterilized under stringent conditions to ensure disinfection. In comparison, disposable medical articles are usually only used once, and even then, disposing procedures are not straightforward, rather they often involve several steps to safeguard against potential hazards. Typically, after use, disposable medical articles must be disinfected or sterilized, adding a significant cost prior to disposal into a specially designated landfill or waste incinerator. As a result, the disposal cost for the contaminated single use articles is quite high.

Despite the high cost of disposal, single use medical articles are desirable because of the assurance of clean, and uncontaminated equipment. Many times in the medical context, sterilization procedures conducted improperly can result in detrimental effects such as the transmission of infectious agents from one patient to another. Improper sterilization can also be disastrous in a laboratory setting, where, for example, contaminated equipment can ruin experiments resulting in tremendous costs of time and money.

Currently, disposable medical fabrics are generally composed of thermoplastic fibers such as polyethylene, polypropylene, polyesters, polyamides and acrylics. They are typically from 10 to 100 grams per square yard in weight and can be woven, knitted or otherwise formed by methods well known to those in the textile arts while the non-wovens can be thermobonded, hydroentangled, wet laid or needle punched and films can be formed by blow or cast extrusion or by solution casting.

The use of polymers for various disposable articles is widespread and well known in the art, In fact the heaviest use of polymers in the form of film and fibers occurs in the packaging and disposable article industries. Films and fibers employed in the packaging industry include those used in food and non-food packaging, merchandise bags and trash bags. In the disposable article industry, the general uses of polymers occurs in the construction of diapers, personal hygiene articles, surgical drapes and hospital gowns, instrument pads, bandages, and protective covers for various objects.

In light of depleting landfill space and inadequate disposal sites, there is a need for polymers, which are water responsive. Currently, although polymers such as polyethylene, polypropylene, polyethylene terephthlate, nylon, polystyrene, polyvinyl chloride and polyvinyldene chloride are popular for their superior extrusion and film and fiber making properties, these polymers are not water responsive. Furthermore, these polymers are generally non-compostable, which is undesirable from an environmental perspective.

Polymers and polymer blends have been developed which are generally considered to be water responsive. These are polymers, which purportedly have adequate properties to permit them to breakdown when exposed to conditions, which lead to composting. Examples of such arguably water responsive polymers include those made from polyethylene oxide, starch biopolymers and polyvinyl alcohol.

Although polymers extruded from these materials have been employed in film and fiber containing articles, many problems have been encountered with their use. Often the polymers are not completely water responsive or compostable. Furthermore, some water responsive polymers may also be unduly sensitive to water, either limiting the use of the polymer or requiring some type of surface treatment to the polymer, often rendering the polymer non-water responsive. Other polymers are undesirable because they have inadequate heat resistance for wide spread use.

Personal care products such as diapers, sanitary napkins, adult incontinence garments, and the like are generally constructed from a number of different components and materials. Such articles usually have some portion, usually the backing layer, constructed of a liquid repellent or non-water responsive polymer material. The non-water responsive material commonly used includes plastic materials such as polyethylene film or copolymers of ethylene and other polar and nonpolar monomers. The purpose of the non-water responsive layer is to minimize or prevent absorbed liquid that may, during use, exude from the absorbent and soil the user or adjacent clothing. The non-water responsive layer also has the advantage of allowing greater utilization of the absorbent capacity of the product.

Although such products are relatively inexpensive, sanitary and easy to use, disposal of a soiled product is not without its problems. Typically, the soiled products are disposed in a solid waste receptacle. This adds to solid waste disposal costs and presents health risks to persons who may come in contact with the soiled product. An ideal disposal alternative would be to use municipal sewage treatment and private residential septic systems by flushing the soiled product in a toilet. Products suited for disposal in sewage systems are termed "flushable." While flushing such articles would be convenient, the non-water responsive material currently used in personal care products normally does not disintegrate in water. This tends to plug toilets and sewer pipes, frequently necessitating a visit from a plumber. At the municipal sewage treatment plant, the non-water responsive material may disrupt operations by plugging screens and causing sewage disposal problems. It therefore becomes necessary, although undesirable, to separate the barrier film material from the absorbent article prior to flushing.

In addition to the article itself, typically the packaging in which the disposable article is distributed is also made from a non-water responsive, specifically water resistant, material. Water resistivity is necessary to prevent the degradation of the packaging from environmental conditions and to protect the disposable articles therein. Although this packaging may be safely stored with other refuse for commercial disposal, and especially in the case of individual packaging of the products, it is often more convenient to dispose of the packaging in the toilet with the discarded disposable article. However, where such packaging is composed of a water resistant material, the aforementioned problems persist.

The use of lactic acid and lactide to manufacture a water responsive polymer is well known in the medical industry. Such polymers have been used in the past for making sutures, clamps, bone plates and biologically active controlled release devices. Processes developed for the manufacture of such polymers to be utilized in the medical industry have incorporated techniques, which respond to the need for high purity and biocompatibility in the final product. These processes, however, are typically designed to produce small volumes of high dollar-value products, with less emphasis on manufacturing cost and yield.

It is generally known that lactide polymers or poly (lactides) are unstable, however, the consequence of this instability has several aspects. One aspect is biodegradation or hydrolysis, which occurs when lactide polymers, or articles manufactured from lactide polymers, are discarded or composted after completing their useful life. Another aspect of such instability is the degradation of lactide polymers during processing at elevated temperatures as, for example, during melt processing by end-user purchasers of polymer resins.

In the medical area there is a predominant need for polymers which are highly stable and therefore desirable for use in medical devices. Such a demand has historically been prevalent in the high value, low volume medical specialty market, but is now also equally prevalent in the low value, high volume medical market.

As described in U.S. Pat. No. 5,472,518, compositions comprised of multilayer polymer films are known in the art. The utility of such structures lies in the manipulation of physical properties in order to increase the stability or lifetime during use of such structure. For example U.S. Pat. No. 4,826,493 describes the use of a thin layer of hydroxybutyrate polymer as a component of a multilayer structure as a barrier film for diaper components and ostomy bags.

Another example of use of multilayer films is found in U.S. Pat. No. 4,620,999 which describes the use of a water soluble film coated with, or laminated to, a water insoluble film as a disposable bag. The patent describes a package for body waste which is stable to human waste during use, but which can be made to degrade in the toilet, at a rate suitable for entry into a sewage system without blockage, by adding a caustic substance to achieve a pH level of at least 12. Such structures usually consist of a polyvinyl alcohol film layer coated with polyhydroxybutryate.

A similar excretion-treating bag allowing discarding in flush toilet or sludge vessel is disclosed in JP 6142127. It is composed of an inner layer of water resistant resin such as polylactide and an outer layer of water soluble polyvinyl alcohol. As disclosed in this patent, there are many examples of multilayer films that are utilized in disposable objects. Most of these examples consist of films or fibers, which are comprised of external layers of an environmentally degradable polymer and an internal layer of water responsive polymer. Typically, the external layers are comprised of polyolefin, polycaprolactone, or ethylene vinyl acetate and the internal layer is comprised of polyvinyl alcohol. These examples, however, are all limited to compositions consisting of multilayers of different polymers, and do not encompass actual blends of different polymers.

Another family of patents, including EP 241178, JP 62223112, and U.S. Pat. No. 4,933,182, describes a controlled release composition for treating periodontal disease. The compositions are comprised of a therapeutically effective agent in a two-phase carrier consisting of a continuous phase and a discontinuous phase. The continuous phase consists of a water soluble polymer and the discontinuous phase consists of a polymer of limited water solubility. Although the compositions of these inventions include the use of more than one polymer, the polymers are utilized in layers and not as intermingled or blended components.

The use of polymer blends for use in water responsive articles is also disclosed in U.S. Pat. Nos. 5,508,101, 5,567, 510, and 5,472,518. This group of patents describes compositions that are designed to be sturdy and resistant to water during storage, preparation and use but dispersible in a commercial laundry cycle. Specifically, the compositions described in the above group of patents are aqueous-alkali dispersible. More specifically, the compositions described in the above group of patents are dispersible in water at conditions of elevated temperature, greater than 50° C., and elevated pH, greater than 7. These compositions dispersed via hydrolytical degradation of the hydrolytically degradable polymer under the specific conditions encountered during a commercial laundry cycle. The compositions described in the above group of patents are not dispersible in cold water and do no lose their integrity when in contact with tap water for more than twenty-four hours. Therefore, there is a need to provide compositions that are at least weakenable, preferably, disintegratable and more preferably, dispersible in ordinary tap water without elevated temperature, without elevated pH and without a laundry cycle.

Further, the compositions of this group consist of articles constructed from polymers, which are first formed into fibers or films and then combined. As such, the compositions are actually mini-layers of the individual polymer films or fibers. Therefore, although the fibers and films of the polymers of such compositions are considered to be in very close proximity with one another, they are not actual polymer blends made by melting the polymers into a homogenous molten mixture. The dispersion of one polymer within another in these compositions, is not viewed as homogenous since the individual polymers are essentially distinct and separate fibers or films.

Polymer blend compositions consisting of fibers and films that are optimally combined are desirable because they are highly stable. Optimal combination of polymers means the polymers of the blend are connected as closely as possible without the requirement of polymerization. Although blended polymer compositions are known, improved polymer blends wherein the fibers and films are more intimately connected are desirable since the resulting composition is then more stable, pliable and versatile.

In addition to the need for polymer compositions that are highly stable, and therefore suitable for regular use in most disposable articles, there is a simultaneous need for such polymer compositions to be cold-water responsive. What is needed therefore, is a material that may be utilized for the manufacture of disposable articles and which is cold-water responsive. Desirably, such a material should be versatile and inexpensive to produce. Additionally, the material should be stable enough for intended use but subject to degradation under predetermined conditions.

SUMMARY OF THE INVENTION

The present invention provides selectively cold-water responsive compositions made from polymers such as polylactide and cold-water soluble polyvinyl alcohol. The present invention also provides methods of making and using cold-water responsive compositions and includes articles comprising the cold-water responsive compositions. Desirably, the articles are designed for a single use and are disposable in cold water by flushing in a toilet.

Products used according to the present invention comprise cold-water responsive polymer compositions. The term "cold-water responsive," as used herein, means that the compositions are either cold-water dispersible, cold-water disintegratable or cold-water weakenable. The degree of cold-water responsiveness may vary depending upon the composition of the polymers, chemical or manufacturing modifications thereto, and the temperature of the water, for example. The compositions of the present invention do not disperse via hydrolytical degradation of a hydrolytically degradable polymer, for example polylactide. The compositions of the present invention are responsive to cold water by the gradual dissolution of a cold-water soluble component in the compositions, for example cold-water soluble polyvinyl alcohol.

Products of the present invention may be constructed of combinations of polymers including, but not limited to: polylactic acid, polyvinyl alcohol, polycapralactone polyhydroxybutryate-co-valorate, polyethylene succinate and polybutylene succinate. A commercial example of polybutylene succinate is sold under the trademark BIONOLLE®. Products of the present invention are constructed of compositions comprising at least one hydrolytically degradable polymer and at least one cold-water soluble polymer. The term "hydrolytically degradable," as used herein, means degradation by hydrolysis. Hydrolytically degradable polymers include, but are not limited to, polylactic acid, polyester amides, polyglycolic acid, and polyhydroxybutyrate-co-valorate and the like; and combinations thereof as copolymers, blends, mixtures and the like.

The term "cold-water soluble," as used herein, means that the polymer will completely dissolve upon extended contact with cold water at temperatures less than about 45° C., preferably at temperatures less than about 25° C. Nonlimiting types of water soluble polymers include polyvinyl alcohol, polyaspartic acid, polyacrylic acid, polymethacrylic acid, polyacrylamide, polyvinyl pyrrolidone, polyalkylene oxides, complex carbohydrates and combinations thereof as copolymers, blends, mixtures, and the like.

The present invention discloses selectively cold-water responsive polymer blend compositions of films and fibers having a wide range of cold-water responsiveness including water dispersible, water disintegratable, water weakenable and water stable. The present invention also discloses methods for the manufacture of cold-water responsive polymer blend compositions useful for manufacturing films and fibers to suit for different application needs. The composition range responsible for each type of water responsiveness is also disclosed. The compositions of the present invention are useful as components in flushable personal care products, such as the outer cover film for diapers, the laminating film for clothlike outer cover, baffle film for feminine pads and pantiliners, etc. In addition to flushability, the compositions of the present invention have the advantage of being biodegradable so that the materials will degrade in anaerobic digesters and aeration tanks in wastewater treatment plants and will not increase the volume of sludge.

These and other features and advantages of the present invention will become apparent after a review of the following detailed description of the disclosed embodiments.

DETAILED DESCRIPTION

Figure 1:
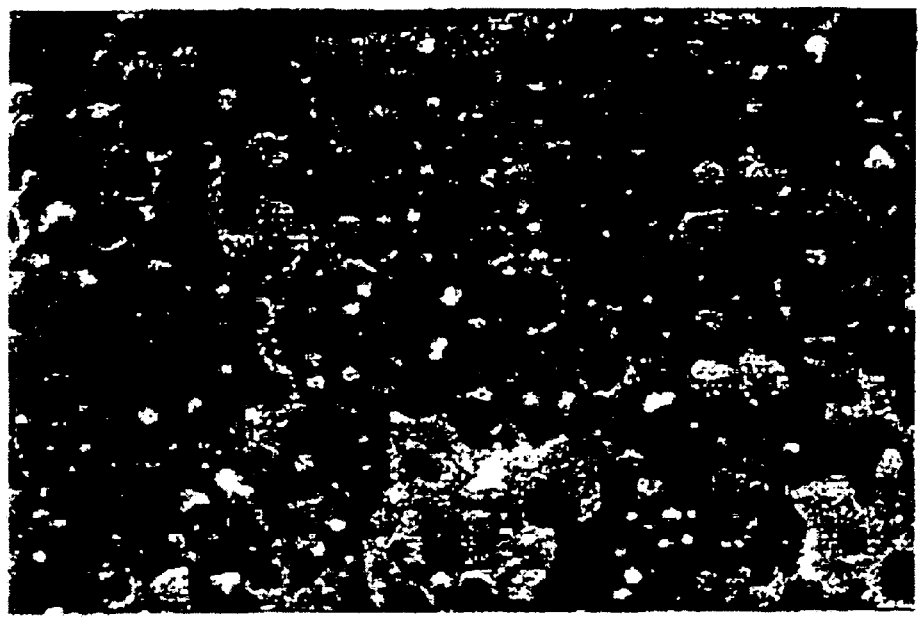
FIG. 1 is SEM photomicrograph of a cross-section of a melt blend of about 30 weight percent polylactic acid and about 70 weight percent polyvinyl alcohol.

The present invention provides selectively cold-water responsive polymer blend compositions of film or fiber-based products configured into such fabrics, garments and articles as drapes, towels, covers, overwraps, gowns, head coverings, face masks, shoe coverings, CSR wraps, sponges, dressings, tapes, underpads, diapers, liners, wash cloths, sheets, pillow covers, napkins, cloth-like outercovers, feminine tampons, pads and pantiliners, and baffle films therefor, and any woven, non-woven, or otherwise formed materials. Such products can be employed in the medical industry both in hospitals, outpatient facilities and in home environments.

Many of these products generally come into contact with human bodily fluids and their disposal and disinfection has become a matter of major concern in light of the lack of biodegradability of prior products and the potential spread of human fluid-born diseases such as hepatitis B and AIDS.

To overcome these difficulties, the present invention provides that products employed in the manufacture of such items be composed of polymer blend compositions, of films or fibers, which are water responsive, either alone or with the addition of surfactants, salts and bleaches. The invention provides that the relative amounts of the polymers and modifiers in the inventive compositions may be adjusted to increase or decrease the solubility of the products made therefrom in water.

The present invention includes compositions and methods for the production of selectively cold-water responsive polymer blends. These water responsive polymer blends are constructed from at least one water soluble polymer and at least one hydrolytically degradable polymers including polylactic acid (PLA), polyvinyl alcohol (PVOH), and polyhydroxybutryate-co-valorate (PHBV). PLA, in the form of lactide copolymers with other cyclic esters, imparts properties such as softness and pliability, and therefore can be used for certain embodiments of the present invention. Cold-water soluble polyvinyl alcohol of a partially hydrolyzed polyvinyl acetate is desired for the compositions of the present invention and typically the hydrolysis level is between approximately 70% and 85%. The term "hydrolysis level" as used herein is defined as the percentage of vinyl acetate units in polyvinyl acetate that is hydrolyzed into vinyl alcohol units in the polyvinyl alcohol. The PHBV resins for the present invention can be made by either the fermentation process of carbohydrate or an organic acid by a microorganism, e.g. *Alcaligenes eutrophus,* or by the use of transgenic plants. ("Biodegradable Plastics from Plants," CHEMTECH, September 1996, ppgs. 38–44).

Depending upon the purpose and use of an article, compositions comprising different components of variable water sensitivity may be desired. Controlling water responsiveness is necessary for different components in certain products due to the location of use in relation to body waste. For example, a diaper backsheet may be desirably water weakenable, whereas the absorbent filler may be desirably water dispersible. The ability to determine and predict the water sensitivity of specific polymer blend compositions is therefore important aspect of the present invention.

The selectively water responsive polymers of the present invention are particularly desirable and unique because of their water responsive qualities. Generally, depending on individual compositions and blends of polymers, as well as the method of manufacture of the blends, the water responsiveness of the resulting material may be manipulated and determined. The degree of water responsiveness that may be determined according to the compositions and methods of the present invention include water dispersible, water disintegratable and water weakenable. Compositions produced from a blend of a hydrolytically degradable polymer and a water soluble polymer may have different morphologies though combined at the same proportion.

Either of the hydrolytically degradable polymer or the water soluble polymer may form the continuous phase depending on the conditions and methods used to produce the blends and the molecular weights, melt viscosities, branching, grafting and linearity of the polymer components. In order to produce cold-water responsive compositions, it is necessary that the cold-water soluble component of the blend form the continuous phase. Thus, the hydrolytically degradable polymer component should form the dispersed phase. The hydrolytically degradable polymer component is desired to improve the mechanical properties and melt processability of the composition. If a water soluble component is the dispersed phase and the a non cold-water soluble polymer is the continuous phase of the composition, the resulting composition is stable in cold water and requires other conditions, such as elevated temperature and pH, for dispersibility as described in U.S. Pat. Nos. 5,472,518, 5,508,101 and 5,567,510. The present invention discloses blend morphologies that provide cold-water responsiveness that are desirably dispersible or disintegratable in toilet water. More importantly, the compositions of the present invention do not require elevated temperature or pH as required in U.S. Pat. Nos. 5,472,518, 5,508,101 and 5,567,510 for responsiveness and dispersibility.

Generally, manufacturers of polymers utilizing standard processes convert raw material monomers into polymer beads, resins or other pelletized or powdered products, which are commercially available from companies such as Aldrich (Milwaukee, Wis.), Dow Chemical (Midland, Mich.), DuPont Company (Wilmington, Del.), Exxon (Baytown, Tex.), Nippon Goshei (Japan) and Union Carbide Corporation (Danbury, Conn.). The polymer in this form may then be used in processes such as extruding, blow-molding, casting films, blowing films, thermoforming, injection molding or fiber spinning at elevated temperatures, for example, to form useful articles. The above processes are collectively referred to as melt processing. Polymers produced by the any process and may be provided commercially as beads, resins powders or other non-finished solid forms. These polymers are also generally referred to as resins.

Desirably, the PVOH incorporated in the compositions of the present invention is cold-water soluble. It is also desirable that the PVOH is thermoplastic. Various grades of such cold-water soluble and thermoplastic PVOHs are commercially available from Nippon Synthetic Chemical Industry Co., Ltd. of Japan. The PVOH employed as the water-soluble component of the embodiments illustrated in the Examples below was obtained from Nippon Synthetic under the tradename ECOMATY AX. The ECOMATY PVOHs have a unique molecular architecture and are cold-water soluble and thermoplastic without the addition of plasticizers. The unique PVOH molecular architecture is that of a branched PVOH comprising structural units of vinyl alcohol, vinyl acetate and polymerized α-olefin. The branched molecular architecture of the ECOMATY PVOHs is considered to be unique. It is believed that the branching reduces the crystallinity of the PVOH and provides improved water solubility, particularly cold-water solubility, melt processability and stability when combined with PLA. The PVOH of the present invention may have different lengths and amounts of branches as long as the PVOH is cold-water soluble.

The melt flow rates of the ECOMATY PVOHs range from 3 g/10 min at 210° C. and 2.16 kg for AX-300, to 4 g/10 min for AX-400TN, to 10 g/10 min for AX-2000 and to 100 g/10 min for AX-10000 at the same conditions. The melting temperatures of the above PVOHs vary form 200 to 210° C. The water solubility of ECOMATY AX-200 at 25° C. is 1.0 $\mu$/sec providing a 1 mil film that will dissolve in water in less than about a half a minute. The properties of the ECOMATY polyvinyl alcohols are described in Nippon Synthetic Industry's product literature entitled "The new age of plastics is here" the disclosure of which is incorporated herein by reference in its entirety.

PLA resins produced by different synthetic methods such as ring-opening polymerization of lactide or direct condensation polymerization from lactic acid are particularly useful for the compositions of the present invention. A PLA ($M_n$=60,000, Tg (glass transition temperature)=60° C., Mw=144,000, 96.8% L-Isomer), purchased from Aldrich Chemical Co., Milwaukee, Wis., was used in the examples. Cold water soluble PVOH (Ecomaty AX 10000), purchased from Nippon Gohsei, Japan, is also an exemplary type resin that was used in the examples.

The hydrolytically degradable and water soluble polymer blend compositions according to the present invention are produced by a melt mixing process. It is desired according to the present invention to blend or mix the two components in an extruder, such as a single-screw or twin-screw extruder under appropriate temperature and shear/pressure conditions to ensure mixing. The blending process can also be performed in a batchwise mixing device, such as a melt mixer or a kneader. PLA or PVOH can be fed into the extruder/mixer either simultaneously or in sequence.

The present invention discloses selectively water responsive homogenous polymer blend compositions comprising hydrolytically degradable and water soluble polymer blend such as polylactide and polyvinyl alcohol. The term "homogeneous polymer blend composition," as used herein, means that the polymer blend forms a cohesive, continuous structure of polylactide and polyvinyl alcohol. A homogenous polymer blend composition can be achieved by the mixing of polylactide and polyvinyl alcohol at temperatures above the melting point of the polymer having the highest melting point, and below the decomposition point of the polymer having the lowest decomposition point, in order to form a homogeneous molten mixture of the polymers (prior to cooling to solid form, e.g. films or fibers). For homogenous polymer blend compositions of polylactide and polyvinyl alcohol, the polymer having the higher melting point is polyvinyl alcohol and the polymer having the lower decomposition point is also polyvinyl alcohol. The melting point for polyvinyl alcohol is generally approximately between 180–190° C., and more specifically around 183° C. The decomposition point of polyvinyl alcohol is above approximately 200° C. The resulting composition resembles islands of polylactide in a sea of polyvinyl alcohol, for example, and at a microscopic level has the appearance of approximately uniform distribution of polylactide among polyvinyl alcohol. The homogeneous polymer blend composition of the present invention therefore has a very fine dispersion of polylactide islands of average size of less than about 0.3–0.4 microns dispersed within polyvinyl alcohol.

Based upon the uniformity of dispersion, the "polymer blend" of the present invention is distinguishable from "blended polymers." The compositions of the present invention comprise polymers that are blended above the melting point of the polymer having the highest melting point (polyvinyl alcohol), and below the decomposition points of the polymer having the lowest decomposition point (polyvinyl alcohol). The homogeneous polymer blend composition, therefore, is formed prior to the polymers being formed into films or fibers, resulting in compositions of polymers which are highly, and intimately interconnected, having a selectively uniform dispersion. Such compositions are distinguishable from those comprising blended polymers that consist of polymers which are blended after they have been formed into fibers or films, resulting in compositions which do not have approximate uniform dispersion and often appearing as individual polymers layered or mixed together. Summarily, when individual polymers are mixed at temperatures above the melting point of the polymer having the highest melting point, and below the decomposition point of the polymer having the lowest decomposition point, an approximately uniform distribution and dispersion of polymers results. In contrast, when individual polymers are mixed according to standard practices, a blended polymer composition results wherein the polymers are not as integrally associated.

The water sensitivity of the polymer compositions may be controlled according to the degree of the homogeneity of the polymer blends. Mixing, shearing, extrusion and other blending techniques, as well as the relative proportions of the polymer resins used, may be manipulated to determine the microstructure of polymer compositions. The 'microstructure' of the polymer blends refers specifically to the size and distribution of polylactide islands within the polyvinyl alcohol sea, for example. The size of the islands may vary from approximately 0.1 to 5.0 $\mu$m. Generally, as the size of the islands increases, and/or as the distance between them decreases, the composition gains greater mechanical strength and loses pliability. For example, for water dispersible compositions, the islands are typically small (approximately 0.2–1.0 $\mu$m), and are distributed so that they are far apart from each other. For water disintegratable compositions, the islands are closer together, with a few islands that may even be connected to one another. For water weakenable compositions, the islands can be in very close proximity and a majority of them appear as large clumps.

The method of making films of the present invention effects the morphology of the film. To form a film of finely dispersed PLA of particles that are spherical, near spherical or ellipsoidal, it is desirable to use a non-orienting method to form the film. On non-orienting method of making films is thermomechanical pressing. An example of thermomechanical pressing is described in the examples below. Orienting methods of making films, such as extruding or blowing films, result in films with in which the dispersed phase has a morphology that contains PLA extended into a fibrous structure through the PVOH continuous phase. Oriented films have reduced water, responsiveness and are not dispersible in cold water but are only cold-water weakenable or cold-water disintegratable. The present invention provides improved compositions and methods of making compositions with improved morphologies and cold-water responsiveness.

One embodiment of the present invention is a homogeneous polymer blend composition comprising from about 1 to about 35 weight percent polylactide and from about 65 to about 99 weight percent polyvinyl alcohol, wherein such composition is water dispersible. The composition is characterized by a morphology of fine PLA particles dispersed in a continuous phase of PVOH. The term "water dispersible," as used herein, means that the composition will dissolve or break into pieces smaller than a 20 mesh after being tested with water at room temperature (18–22° C.) for 2 minutes. "Testing with water," as used herein, means preparing a sample of the composition then immersing it into a scintillation vial filled with water for 5 minutes, followed by shaking the vial for approximately 30 seconds in a mechanical shaking device, and then emptying the contents of the vial through a standard 20 mesh screen.

Another embodiment of the present invention is a homogeneous polymer blend composition comprising from about 35 to about 45 weight percent polylactide and from about 65 to about 55 weight percent polyvinyl alcohol, wherein such composition is water disintegratable. This composition is also characterized by a morphology of fine PLA particles dispersed in a continuous phase of PVOH. The term "water disintegratable" as used herein, means that the composition will break into multiple pieces after 2 minutes and that some of the composition pieces will be caught by a 20 mesh screen.

One other embodiment of the present invention is a composition comprising from about 45 to about 55 weight percent polylactide and from about 55 to about 45 weight percent polyvinyl alcohol, wherein such composition is water weakenable. The composition is characterized by a morphology of fine PLA particles dispersed in a continuous phase of PVOH. The term "water weakenable," as used herein, means that the composition remains in one piece but weakens and loses rigidity after 5 minutes and becomes drapeable, i.e., it bends without an external force applied to the composition when it is held by one corner at a horizontal position. The term "water stable", as used herein, means that the composition does not become drapeable and remains in one piece after testing with water.

The compositions of the present invention may be formed into polymer fibers or into polymer films.

A method of making a selectively water sensitive homogenous polymer blend composition, comprises combining hydrolytically degradable polymers, such as polylactide, and water soluble polymers, such as polyvinyl alcohol, at a temperature above the melting point of the polymer having the highest melting point, and below the decomposition point of the polymer having the lowest decomposition point, to form a homogeneous polymer blend composition.

For making a composition that is selectively water dispersible, approximately 1–35% polylactide and approximately 65–99% polyvinyl alcohol are combined. For making a composition that is selectively water-disintegratable, approximately 35–45% polylactide and approximately 65–55% polyvinyl alcohol are combined. For making a composition that is selectively water-weakenable, approximately 45–55% polylactide and approximately 55–45% polyvinyl alcohol are combined. For making a composition that is selectively water stable, approximately 55–99% polylactide and approximately 45–1% polyvinyl alcohol are combined.

Processing characteristics of the polymer blends for films can be enhanced by the optional incorporation of lubricants or slip agents into the blends. Such lubricants are well known in the art and include TWEEN 20, TURGITOL NP 13 available from Union Carbide Corporation (Danbury, Conn.) and various fatty acids such as KENAMIDE E available from Witco Chemical (USA). In addition, the blends may contain other components to enhance the properties of the resulting material. For example, polyethylene glycol can be added to lower the melt viscosity of the melted blend to a range suitable for other processes such as meltblown or meltsprayed nonwoven materials. Suitable polyethylene glycols are available from Union Carbide under the trade name CARBOWAX®.

Polymer blending is an important aspect of the manufacture of the present invention compositions. Depending upon parameters such as the selection of blending techniques, temperature profiles, and pressure applications, the final water responsive qualities of the compositions may be affected.

The polymer blending process for water responsive compositions containing hydrolytically degradable polymers, such as PLA, and water soluble polymers, such as PVOH, desirably involves the use of an extruder. Desirably, the two polymer components are blended or mixed in an extruder such as a single-screw or a twin-screw extruder under appropriate temperature and shear/pressure conditions. The blending process can also be performed in batchwise mixing devices such as a melt mixer or a kneader. Both PVOH and PLA can be fed to an extruder either simultaneously or in sequence to minimize any adverse effects on the polymers such as degradation or discoloration.

The present invention is further illustrated by the following examples, which are not to be construed in any way as imposing limitations upon the scope of the claims. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

For the following examples, a section of the prepared film was cut measuring about ¼ of an inch by about ½ of an inch. The cold-water response test involved using a pair of tweezers to hold the section of the film, immersing it into a scintillation vial filled with 20 milliliters of water at about 20° C. and holding it there for 5 minutes. After 5 minutes, the cap was placed on the scintillation vial and the vial was placed in a Model 75 Shaker (available from Burrell Corp., Pittsburgh, Pa.). The vial was shaken for 30 seconds with the shaker set a maximum speed. If the film began to disperse or disintegrate, the contents of the scintillation vial were emptied through a 20 mesh screen (20 mesh U.S.A. Standard Testing Sieve, ASTM Standard E-11 Specification, No. 20). The vial was then rinsed with 20 milliliter of water from a squeeze bottle to remove any remaining film pieces and emptied through the sieve.

If the film did not disperse or disintegrate, the film was observed for any loss in rigidity.

EXAMPLE 2

A blend containing 21 grams of polylactide and 49 grams of polyvinyl alcohol was prepared using a Haake Rheomix 600 twin-roller mixer (available from Haake, Paramus, N.J.). Each zone of the Haake mixer was preheated to 180° C. The polymer melt temperature after 5 minutes was about 184° C. The material was mixed for 5 minutes at a screw speed of 150 rpm. After 5 minutes, the melt was removed from the mixer and cooled in air. A film (approximately 5 mil thick) was prepared from the composition using a Carver hot press with two heated platens at a temperature of 190° C. and a pressure of 15000 psi for 1 minute.

The film was determined to be cold-water dispersible under the cold-water response test described in Example 1 above.

EXAMPLE 3

A blend containing 28 grams of polylactide and 42 grams of polyvinyl alcohol was prepared using a Haake Rheomix 600 twin-roller mixer (available from Haake, Paramus, N.J.). Each zone of the Haake mixer was preheated to 180° C. The polymer melt temperature after 5 minutes was about 196° C. The material was mixed for 5 minutes at a screw speed of 150 rpm. After 5 minutes, the melt was removed from the mixer and cooled in air. A film (approximately 5 mil thick) was prepared from the composition using a Carver hot press with two heated platens at a temperature of 190° C. and a pressure of 15000 psi for 1 minute.

The film was determined to be cold-water disintegratable under the cold-water response test.

EXAMPLE 4

A blend containing 35 grams of polylactide and 35 grams of polyvinyl alcohol was prepared using a Haake Rheomix 600 twin-roller mixer (available from Haake, Paramus, N.J.). Each zone of the Haake mixer was preheated to 180° C. The polymer melt temperature after 5 minutes was about 196° C. The material was mixed for 5 minutes at a screw speed of 150 rpm. After 5 minutes, the melt was removed from the mixer and cooled in air. A film (approximately 5 mil thick) was prepared from the composition using a Carver hot press with two heated platens at a temperature of 190° C. and a pressure of 15000 psi for 1 minute.

The film was determined to be cold-water weakenable under the cold-water response test.

EXAMPLE 5

A blend containing 42 grams of polylactide and 28 grams of polyvinyl alcohol was prepared using a Haake Rheomix 600 twin-roller mixer (available from Haake, Paramus, N.J.). Each zone of the Haake mixer was preheated to 180° C. The polymer melt temperature after 5 minutes was about 189° C. The material was mixed for 5 minutes at a screw speed of 150 rpm. After 5 minutes, the melt was removed from the mixer and cooled in air. A film (approximately 5 mil thick) was prepared from the composition using a Carver hot press with two heated platens at a temperature of 190° C. and a pressure of 15000 psi for 1 minute.

The film was determined to be cold-water weakenable under the cold-water response test.

EXAMPLE 6

A resin mixture of 20/80 PLA/PVOH, by weight, was added to a Haake TW-100 twin-screw extruder with counter-rotating conical screws mixer (available from Haake, Paramus, N.J.) at 10 lb/hr. The polymer melt temperature during the extrusion was about 186° C. The barrel set temperatures were 170° C., 180° C., 180° C. and 168° C. The screw speed was 150 rpm. Melt strands were cooled by air on a conveyor belt and pelletized. A thin film was prepared under the same conditions as Example 2.

The film was determined to be cold-water dispersible under the cold-water response test.

EXAMPLE 7

A resin mixture of 30/70 PLA/PVOH, by weight, was added to a Haake TW-100 twin-screw extruder with counter-rotating conical screws mixer (available from Haake, Paramus, N.J.) at 10 lb/hr. The polymer melt temperature during the extrusion was about 187° C. The barrel set temperatures were 170° C., 180° C., 180° C. and 168° C. The screw speed was 150 rpm. Melt strands were cooled by air on a conveyor belt and pelletized. A thin film was prepared under the same conditions as Example 2.

The film was determined to be cold-water dispersible under the cold-water response test. A cross-section of a film made from a 30/70 blend of PLA/PVOH was examined under by scanning electron microscopy (SEM). A photomicrograph of the cross-section is shown in FIG. 1. The photomicrograph illustrates the "islands-in-the-sea" morphology that is characteristic of compositions of the present invention. The continuous phase is comprised of a water soluble polymer, namely polyvinyl alcohol. The discontinuous phase is comprised of discrete islands of hydrolytically degradable polymer, namely polylactic acid, of about 0.3 to 0.4 microns average diameter. This islands-in-the-sea morphology provides the blend with responsiveness to tap water at ambient conditions, particularly ambient temperature and pH. This 30/70 blend is water dispersible at room temperature and neutral pH. Increasing or decreasing the relative amount of cold-water soluble polymer incorporated in the blend can alter the cold-water responsiveness of the blend and resulting compositions and articles made therefrom.

EXAMPLE 8

A second film of a 30/70 blend of PLA/PVOH was prepared. However, this second film was prepared from a blend of a grafted polylactic acid. Grafted polylactic compositions and methods of making grafted polylactic compositions are disclosed in copending applications U.S. Ser. Nos. 08/903,864 and 08/903,862 which are incorporated by reference herein in their entirety.

Figure 2:
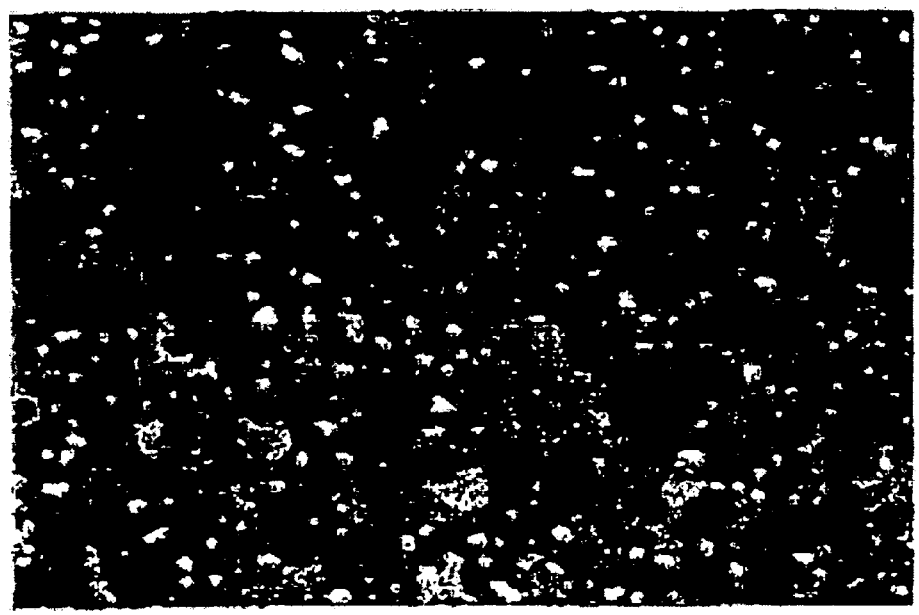
FIG. 2 is SEM photomicrograph of a cross-section of a melt blend of about 30 weight percent of a grafted polylactic acid and about 70 weight percent polyvinyl alcohol.

This film was also determined to be cold-water dispersible under the water response test. A cross-section of a film made from this 30/70 blend of grafted-PLA/PVOH was examined under by scanning electron microscopy (SEM). A photomicrograph of the cross-section is shown in FIG. 2. The photomicrograph also illustrates the "islands-in-the-sea" morphology that is characteristic of compositions of the present invention. However, this blend of grafted PLA has significantly reduced domain size of the grafted PLA islands. The average diameters of the islands of this composition comprising grafted PLA is in the range of about 0.1 to 0.2 microns. The reduction in domain size demonstrates that grafted PLA has improved compatibility with PVOH compared to the ungrafted PLA of the previous examples. This improved compatibility with PVOH was not expected. Additionally, blends comprising grafted PLA and PVOH have improved mechanical properties and improved melt processability which was also not expected. Particularly, improved melt processability is observed during melt processing of materials comprising the grafted PLA.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

What is claimed is:

1. A method of making a selectively cold-water responsive homogenous polymer blend composition, comprising melt blending at least 1 weight percent polylactide and at least 45 weight percent of cold water soluble polyvinyl alcohol at a temperature above the melting point of polyvinyl alcohol, and below the decomposition temperature of polyvinyl alcohol, to form a homogeneous polymer blend composition that is either weakenable, disintegratable or dispersible in water at ambient temperature, wherein the cold water soluble polyvinyl alcohol is soluble in water at 25° C.;

wherein the average pore size of the islands of polylactide varies from approximately 0.1 to approximately 5.0 micrometers.

2. The method of claim 1, wherein the polyvinyl alcohol and the polylactide are melt blended at temperatures ranging from about 180° C. to about 200° C.

3. The method of claim 1, wherein approximately 1–35% by weight polylactide and approximately 65–99% by weight polyvinyl alcohol are combined based on the weight of the polylactide and the polyvinyl alcohol, and wherein such composition is selectively cold water dispersible.

4. The method of claim 1, wherein the composition comprises approximately 35–45% by weight polylactide and approximately 65–55% by weight polyvinyl alcohol based on the weight of the polylactide and the polyvinyl alcohol, and wherein such composition is selectively cold water disintegratable.

5. The method of claim 1, wherein the composition comprises approximately 45–55% by weight polylactide and approximately 55–45% by weight polyvinyl alcohol based on the weight of the polylactide and the polyvinyl alcohol, and wherein such composition is selectively cold water weakenable.

* * * * *